(12) United States Patent
Wang (10) Patent No.: US 10,729,411 B2
(45) Date of Patent: Aug. 4, 2020

(54) SMART TOILET CAPABLE OF MONITORING EXCREMENT AND URINE

(71) Applicant: Zhongtang Wang, Xiamen (CN)

(72) Inventor: Zhongtang Wang, Xiamen (CN)

(73) Assignee: Xiamen Brana Design Co., Ltd., Xiamen (CN)

( * ) Notice: Subject to any disclaimer, the term of this patent is extended or adjusted under 35 U.S.C. 154(b) by 362 days.

(21) Appl. No.: 15/762,563

(22) PCT Filed: Sep. 24, 2015

(86) PCT No.: PCT/CN2015/090489
§ 371 (c)(1),
(2) Date: Mar. 23, 2018

(87) PCT Pub. No.: WO2017/049516
PCT Pub. Date: Mar. 30, 2017

(65) Prior Publication Data
US 2018/0271501 A1    Sep. 27, 2018

(51) Int. Cl.
*A61B 10/00*    (2006.01)
*G01N 33/483*    (2006.01)
*E03D 9/00*    (2006.01)
*G01G 19/00*    (2006.01)
*G01N 1/28*    (2006.01)
*G01N 33/493*    (2006.01)
*E03D 11/02*    (2006.01)

(52) U.S. Cl.
CPC ........ *A61B 10/0038* (2013.01); *A61B 10/007* (2013.01); *E03D 9/00* (2013.01); *G01G 19/00* (2013.01); *G01N 1/286* (2013.01); *G01N 1/2813* (2013.01); *G01N 33/483* (2013.01); *G01N 33/4833* (2013.01); *G01N 33/493* (2013.01); *E03D 11/02* (2013.01)

(58) Field of Classification Search
CPC .............. A61B 10/007; A61B 10/0038; G01N 33/483; G01N 33/4833
See application file for complete search history.

(56) References Cited

U.S. PATENT DOCUMENTS 4,860,767 A * 8/1989 Maekawa ............... E03D 11/00
600/573

FOREIGN PATENT DOCUMENTS

JP    2007205818 A * 8/2007

* cited by examiner

*Primary Examiner* — Daniel L Cerioni
*Assistant Examiner* — Raymond P Dulman (57) ABSTRACT

A smart toilet capable of monitoring excrement and urine comprises a toilet bowl, a toilet seat, a telescopic lifting device, an excrement sample collection device, an excrement specimen preprocessing device, an excrement sample detection and analysis device, a telescopic lighting and photographing device, and a smart terminal. The whole process of bowel movement can be monitored to observe the general characteristics of the excrement and the presence or absence of parasites or eggs and to weigh the excrement, thereby realizing the automatic collection of an excrement sample and the pretreatment of the excrement specimen to provide convenience for the hospital users.

3 Claims, 6 Drawing Sheets

SMART TOILET CAPABLE OF MONITORING EXCREMENT AND URINE

BACKGROUND OF THE INVENTION

Field of the Invention

The present invention relates to a human health testing device, and more particularly to a smart toilet capable of monitoring excrement and urine for monitoring bowel movement, the weight and appearance of the excrement, presence or absence of parasites or eggs, blood composition, pH, bile composition and food composition of the excrement.

Description of the Prior Art

While the incidence of malignant tumor continues to rise worldwide, the incidence and mortality rate for malignant tumors, especially gastrointestinal tumor, in China are higher than the global averages. A study done by the National Central Cancer Registry in 2013 shows that there are over three million new cancer cases each year and gastrointestinal tumor accounts for 43.3% of the overall incidence rate for cancer.

There are no specific symptoms for early-stage gastrointestinal tumor until it has progressed to intermediate or advanced stage. The cure rate for early stage gastrointestinal tumor is high but the mortality rate is high in the intermediate and advanced stages, and involves more complications, poor survival and quality of life, and higher costs. Due to the cancer mortality rate in intermediate and advanced stages, the best chance is early detection and treatment.

The diagnosis and treatment of early stage gastrointestinal tumor are dependent on cancer screening. With massive resources directed towards gastrointestinal tumor and promotion of cancer screening worldwide, there has been a slight improvement in the diagnosis and treatment of early stage gastrointestinal tumor. The diagnosis rate for early stage gastrointestinal tumor is 20% in the United States and 12.5% in Japan but under 10% in China's tertiary hospitals.

The methods of diagnosis for gastrointestinal tumor include: (1) fecal occult blood test; (2) gastrointestinal endoscopy; (3) molecular biology techniques. In particular, fecal occult blood test is non-traumatic, non-invasive, simple and sensitive. Gastrointestinal endoscopy is reliable but is an invasive/traumatic operation requiring special equipment and is not available for screening of general population. Molecular biology tests may be automated and done in large batches but blood must be drawn and completed in a hospital laboratory. The positive rate for fecal occult blood test is up to 95%, making it the top choice for gastrointestinal tumor screening.

Furthermore, bowel movement is closely related to gastrointestinal functions. Fecal testing enables detection of gastrointestinal inflammation and ulcer bleeding, indirectly leading to determination of gastrointestinal, pancreatic and liver/gallbladder functions, and irregularity in intestinal flora, aiding in diagnosis of communicable intestinal diseases.

As one of the greatest inventions in human history, the toilet bowl has significantly reduced communicable gastrointestinal diseases. It could become an intelligent micro-lab. The daily testing of key components in stools helps to monitor household members' gastrointestinal tumor, ulceration, irregular intestinal functions, obstruction of biliary tract, hemolytic diseases and parasitic infection. With advances in IoT technology, the toilet bowl will attract increasing attention as it becomes a key node for health monitoring.

Although the clinical value of fecal test is significant, patients' willingness to obtain stool sample for testing is low. Moreover, fecal testing is a highly manual process. It is difficult to recruit lab technicians to handle the filthy and smelly stool samples, and lab technicians also find it difficult to focus on their job, inadvertently leading to the loss of valuable information in the samples.

In view of the above, an application for a smart toilet capable of monitoring excrement and urine is filed to provide convenience for ordinary users and hospital users.

SUMMARY OF THE INVENTION

The primary object of the present invention is to provide a smart toilet capable of monitoring excrement and urine for improving the working conditions of laboratory personnel, which can daily monitor the user's bowel movement, gastrointestinal tumor, ulceration, irregular intestinal functions, obstruction of biliary tract, hemolytic diseases and parasitic infection, etc., to evaluate gastrointestinal health and provide the user with health or medical advice.

In order to achieve the aforesaid object, the present invention adopts the following technical solution:

The present invention relates to a smart toilet capable of monitoring excrement and urine, comprising a toilet bowl, a toilet seat, a telescopic lifting device, an excrement sample collection device, an excrement specimen preprocessing device, an excrement sample detection and analysis device, a telescopic lighting and photographing device, and a smart terminal;

the telescopic lifting device, the excrement sample collection device, the excrement specimen preprocessing device and the excrement sample detection and analysis device being installed in a space behind a toilet bowl body of the toilet bowl and above a suction channel;

the toilet seat including a flip-type toilet seat cover, a flip-type seat and a smart control panel; one end of each of the flip-type toilet seat cover and the flip-type seat being hingedly connected to the toilet bowl body of the toilet bowl, a user identification system being provided in the small control panel; the telescopic lifting device, the excrement sample collection device, the excrement specimen preprocessing device and the excrement sample detection and analysis device being connected with the smart control panel of the toilet seat through data cables;

the telescopic lighting and photographing device being mounted to a rear side of the flip-type seat;

the smart terminal receiving data transmitted from a data processor through a wireless transmission and performing analysis and interpretation;

the telescopic lifting device including a tray, a telescopic mechanism and an electronic weighing scale; the tray being mounted on a top of the electronic weighing scale, the electronic weighing scale being mounted on an outer end of the telescopic mechanism, an inner end of the telescopic mechanism being fixed in the space behind the toilet bowl body of the toilet bowl, the outer end of the telescopic mechanism, equipped with the tray, passing through a hole that can be opened and closed on a rear wall of the toilet bowl body and extending to a position above the surface of the residual water in the toilet bowl;

the excrement sample collection device including a telescopic connecting arm and a hollow semi-circular tube with a sensor; the hollow semi-circular tube being installed at a front end of the telescopic connecting arm, the hollow semi-circular tube being located above the tray of the telescopic lifting device, a rear end of the telescopic connecting arm being fixed in the space behind the toilet bowl body of the toilet bowl;

the excrement specimen preprocessing device including a sample container, a stirrer and a water injection pipe; the sample container being located at a distal end of a movement path of the hollow semi-circular tube of the excrement sample collection device so as to receive excrement; the stirrer having rotatable stirring blades mounted in the sample container, one end of the water injecting pipe extending into the sample container, another end of the water injecting pipe being connected to a water source;

the excrement sample detection and analysis device including the data processor, an integrated test film, a spectrum scanning analyzer, a robot, a test film storage container and a waste container; the data processor, the integrated test film, the spectrum scanning analyzer, the robot, the test film storage container, the waste container and the robot being installed in the space behind the toilet bowl body of the toilet bowl, a first working position of the robot being located at the test film storage container on which the integrated test film is placed, a second working position of the robot being located at the sample container of the excrement specimen preprocessing device, a third working position of the robot being located at the spectrum scanning analyzer, a fourth working position of the robot being located at the waste container, the robot moving among the four working positions; the spectrum scanning analyzer being connected to the data processor through one of the data cables for providing a scanning image to the data processor.

The integrated test film consists of test papers for pH level, occult blood, stercobilin, stercobilinogen, stercobilirubin, fat droplet, starch and dextrin.

The present invention further comprises an excrement sample automatic cleaning device. The excrement sample automatic cleaning device is installed in the space behind the toilet bowl body of the toilet bowl and above the suction channel. The excrement sample automatic cleaning device is connected to the smart control panel of the toilet seat through one of the data cables and connected to the water storage tank of the toilet bowl through a pipe.

With the above solution, the invention includes an excrement sample collection device, a sample container, an excrement specimen preprocessing device, and an excrement sample detection and analysis device. The excrement sample collection device is used to directly collect an excrement sample. The excrement specimen preprocessing device and the excrement sample detection and analysis device are used to process and analyze the excrement and to obtain the information on whether the user is suspected of having gastrointestinal tumor, ulceration, irregular intestinal functions, obstruction of biliary tract, hemolytic diseases and parasitic infection, etc., providing more comfortable and convenient facilities for the checking of the patient's excrement and improving the willingness to check the patient's excrement. The invention can monitor bowel movement throughout the whole process, which is beneficial for the clinician to obtain the dynamic data, and can avoid the unpleasantness caused by the dirty and odor when the excrement is sent for checking. The test personnel can complete the general checking, chemical checking and microscope checking of the patent's excrement without touching the excrement. The invention can improve the working conditions of laboratory personnel and provide convenience for hospital users.

Embodiments of the present invention will now be described, by way of example only, with reference to the accompanying drawings.

DETAILED DESCRIPTION OF THE PREFERRED EMBODIMENTS

Figure 1:
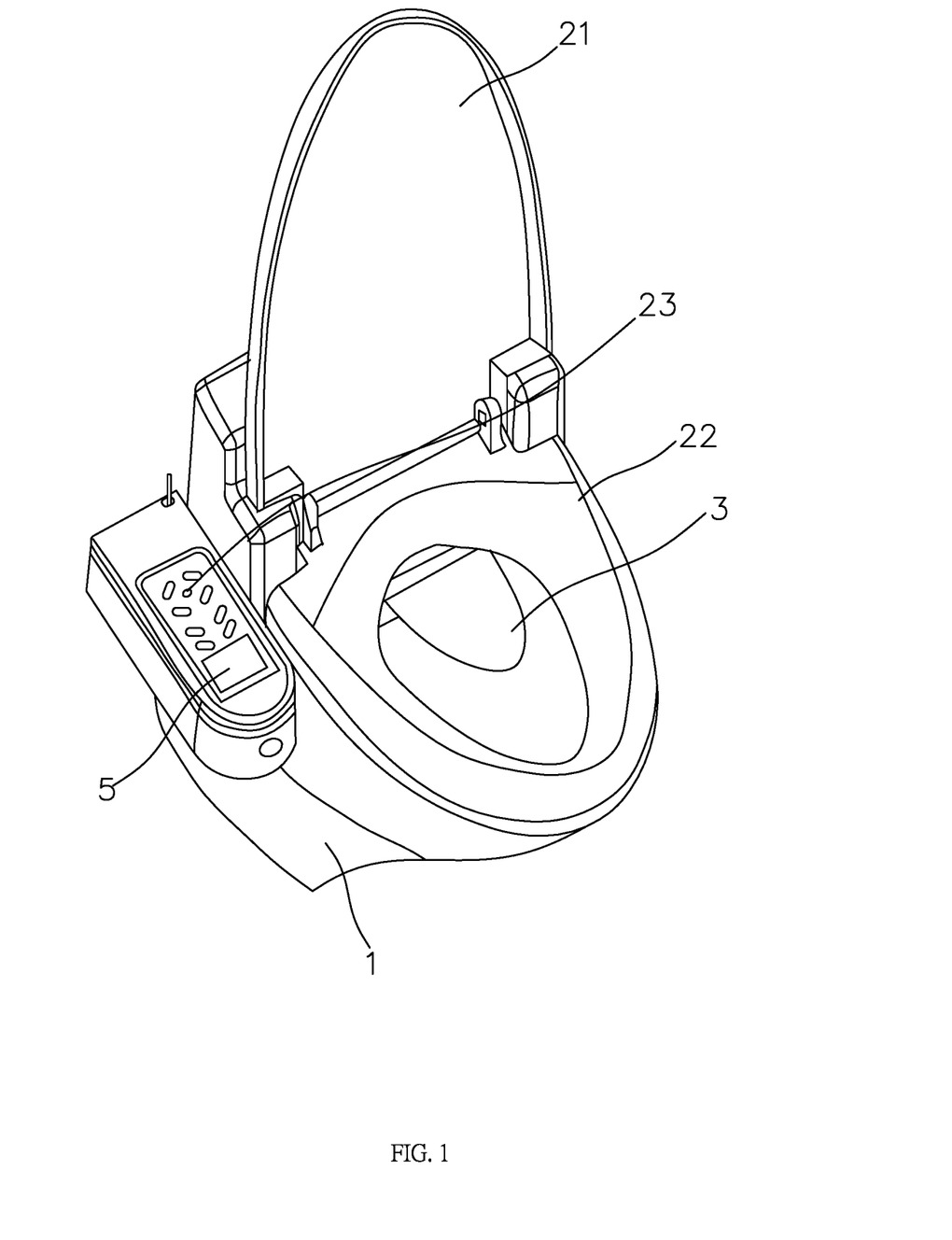
FIG. 1 is a perspective view of the present invention.
Figure 2:
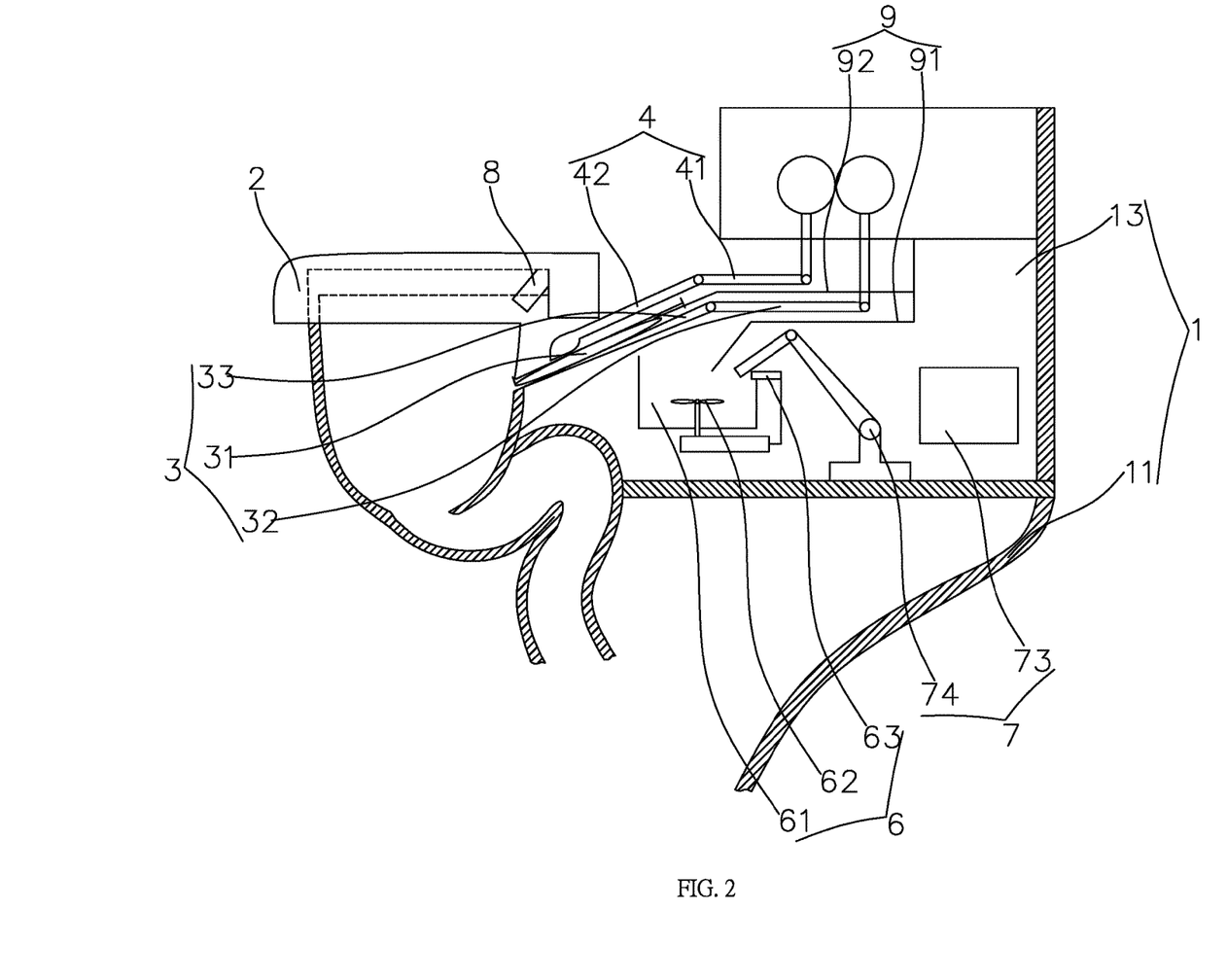
FIG. 2 is a sectional view of the present invention.

As shown in FIG. 1 and FIG. 2, the present invention discloses a smart toilet capable of monitoring excrement and urine, comprising a toilet bowl 1, a toilet seat 2, a telescopic lifting device 3, an excrement sample collection device 4, a smart terminal 5, an excrement specimen preprocessing device 6, an excrement sample detection and analysis device 7, a telescopic lighting and photographing device 8, and an excrement sample automatic cleaning device 9.

The toilet bowl 1 includes a toilet bowl body 11, a suction channel, and a water storage tank 13. The telescopic lifting device 3, the excrement sample collection device 4, the excrement specimen preprocessing device 6, the excrement sample automatic cleaning device 9 and the excrement sample detection and analysis device 7 are all installed in a space behind the toilet bowl body 11 of the toilet bowl 1 and above the suction channel.

The toilet seat 2 includes a flip-type toilet seat cover 21, a flip-type seat 22, and a smart control panel 23. One end of each of the flip-type toilet seat cover 21 and the flip-type seat 22 is hingedly connected to the toilet bowl body 11 of the toilet bowl 1. A user identification system is provided in the small control panel 23. The telescopic lifting device 3, the excrement sample collection device 4, the excrement specimen preprocessing device 6 and the excrement sample detection and analysis device 7 are all connected with the smart control panel 23 of the toilet seat 2 through data cables. The toilet seat 2 is provided with a wireless control device, which is convenient for the user to implement the operation control function of the smart control panel 23 through the smart terminal.

The telescopic lighting and photographing device 8 is mounted to the rear side of the flip-type seat 22. The rear side of the flip-type seat 22 is provided with the built-in telescopic lighting and photographing device.

The smart terminal 5 receives data transmitted from a data processor through a wireless transmission, performs analysis and interpretation, proposes health guidance, and shares the data with a professional healthcare institution.

The telescopic lifting device 3 includes a tray 31, a telescopic mechanism 32, and an electronic weighing scale 33. The tray 31 is mounted on the top of the electronic weighing scale 33. The electronic weighing scale 33 is mounted on the outer end of the telescopic mechanism 32. The inner end of the telescopic mechanism 32 is fixed in the space behind the toilet bowl body 11 of the toilet bowl 1. The outer end of the telescopic mechanism 32, equipped with the tray 31, passes through a hole that can be opened and closed on the rear wall of the toilet bowl body 11 and extend to a position of 2 cm higher than the surface of the residual water in the toilet bowl.

The excrement sample collection device 4 includes a telescopic connecting arm 41 and a hollow semi-circular tube 42 with a sensor. The hollow semi-circular tube 42 is installed at the front end of the telescopic connecting arm 41, and the hollow semi-circular tube 42 is located above the tray 31 of the telescopic lifting device 3 for sucking/scraping excrement. The rear end of the telescopic connecting arm 41 is fixed in the space behind the toilet bowl body 11 of the toilet bowl 1.

The excrement specimen preprocessing device 6 includes a sample container 61, a stirrer 62, and a water injection pipe 63. The sample container 61 is located at the distal end of the movement path of the hollow semi-circular tube 42 of the excrement sample collection device 4 so as to receive excrements. The stirrer 62 has rotatable stirring blades mounted in the sample container 61. One end of the water injecting pipe 63 extends into the sample container 61, and another end of the water injecting pipe 63 is connected to a water source. The power device of the stirrer 62 is connected to the water injection control structure of the water injection pipe 63. When the stirrer 62 is working, it is sensed whether the excrement sample is even. When the excrement is not even, the water is injected. When the excrement sample is even, the water injection is stopped and the stirrer is stopped.

The excrement sample automatic cleaning device 9 includes a flush tray 91 and a flush stirring mechanism 92. The flush stirring mechanism 92 is disposed above the flush tray 91.

Figure 3:
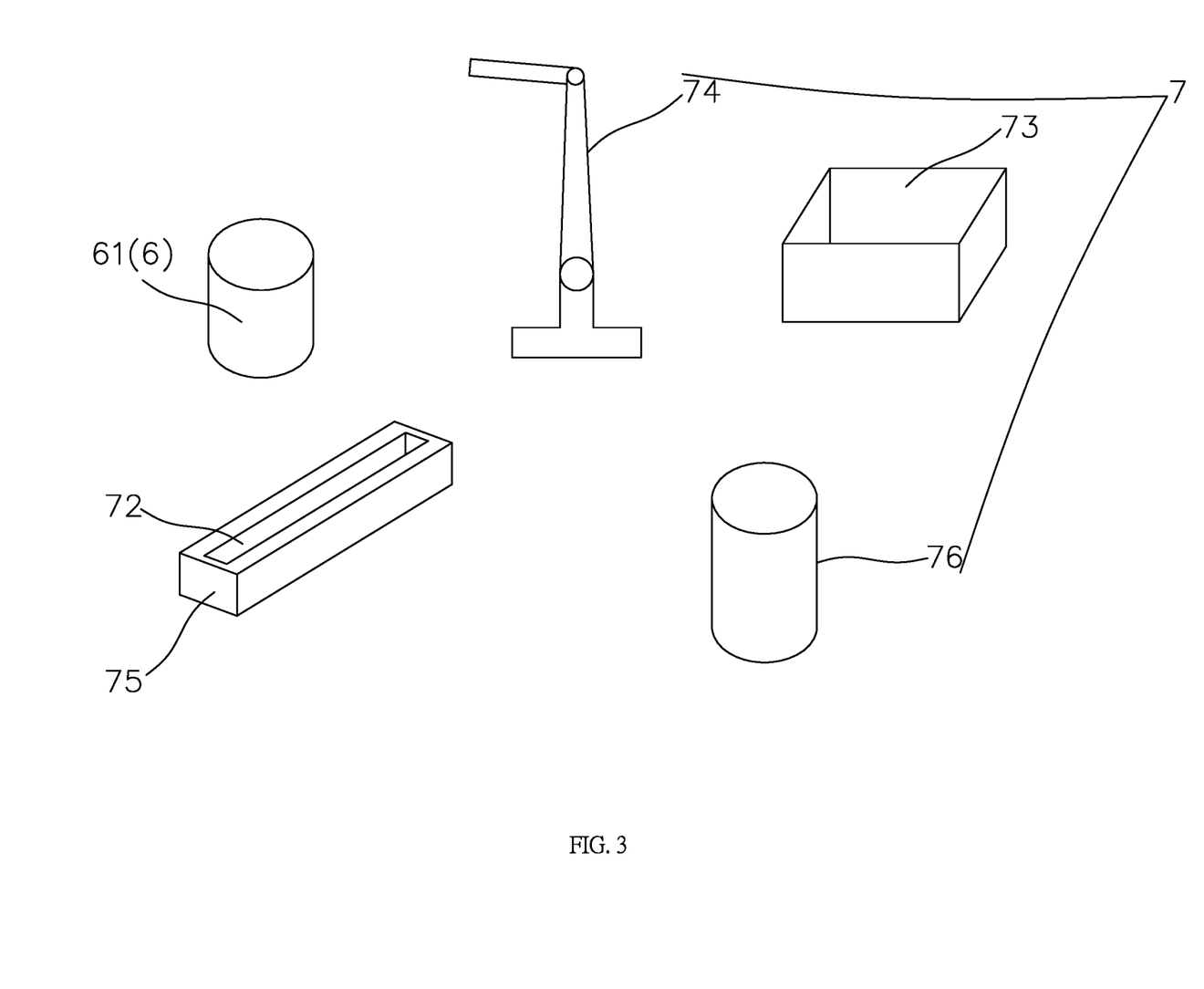
FIG. 3 is an exploded view of the excrement sample detection and analysis device of the present invention.

As shown in FIG. 2 and FIG. 3, the excrement sample detection and analysis device 7 includes a data processor (not shown), an integrated test film 72, a spectrum scanning analyzer 73, a robot 74, and a test film storage container 75, and a waste container 76. The data processor, the integrated test film 72, the spectrum scanning analyzer 73, the robot 74, the test film storage container 75 and the waste container 76 are all installed in the space behind the toilet bowl body 11 of the toilet bowl 1. The first working position of the robot 74 is located at the test film storage container 75 on which the integrated test film 72 is placed. The second working position of the robot 74 is located at the sample container 61 of the excrement specimen preprocessing device 6. The third working position of the robot 74 is located at the spectrum scanning analyzer 73. The fourth working position of the robot 74 is located at the waste container 76. The robot 74 moves among the four working positions. The spectrum scanning analyzer 73 is connected to the data processor through a data cable to provide a scanning image to the data processor. The spectrum scanning analyzer 73 includes a multi-channel grating that matches the chromogenic reaction of the test film. The data processor includes detection data storage, analysis processing, and transmission elements.

Figure 4:
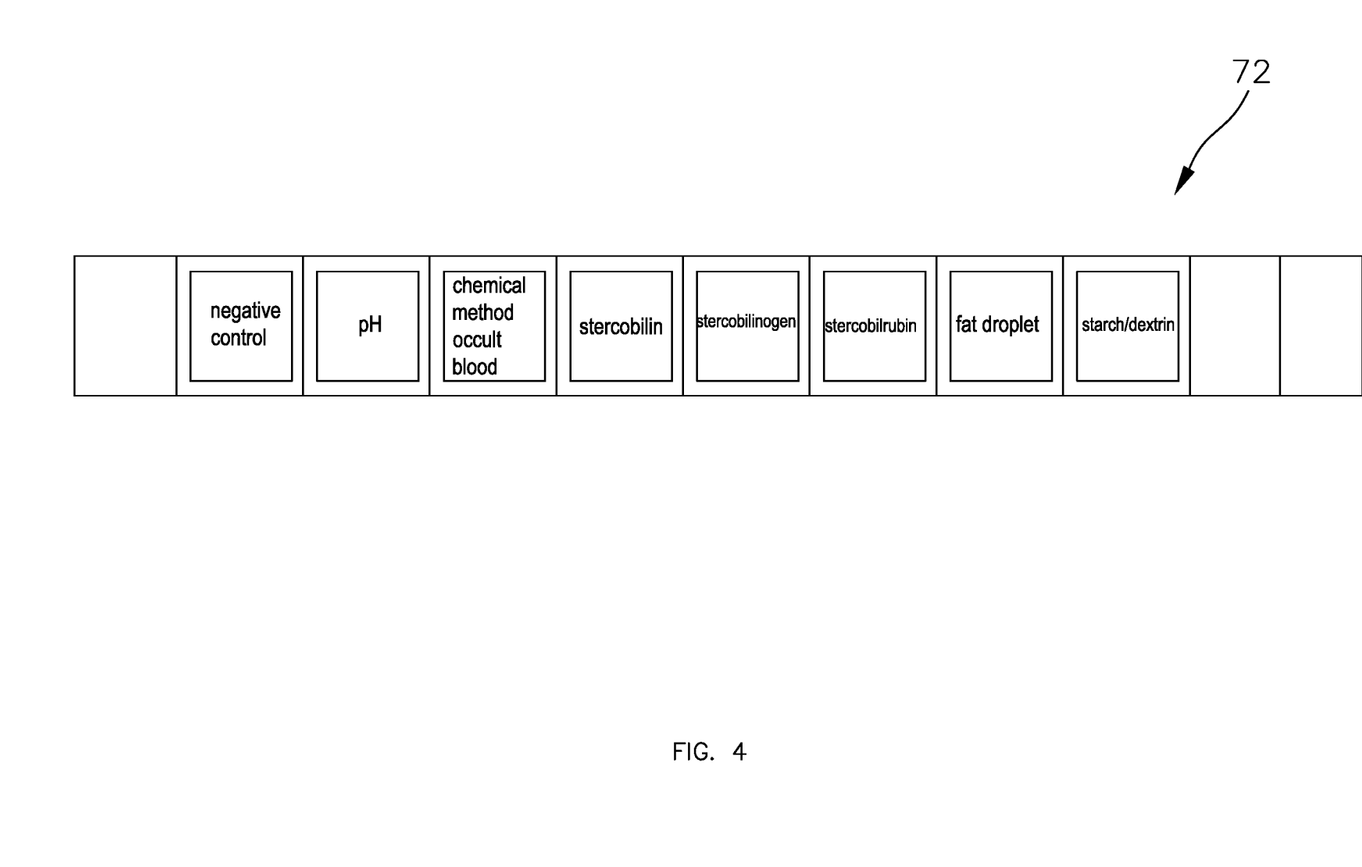
FIG. 4 is a schematic view of a first example of the integrated test film of the present invention.
Figure 5:
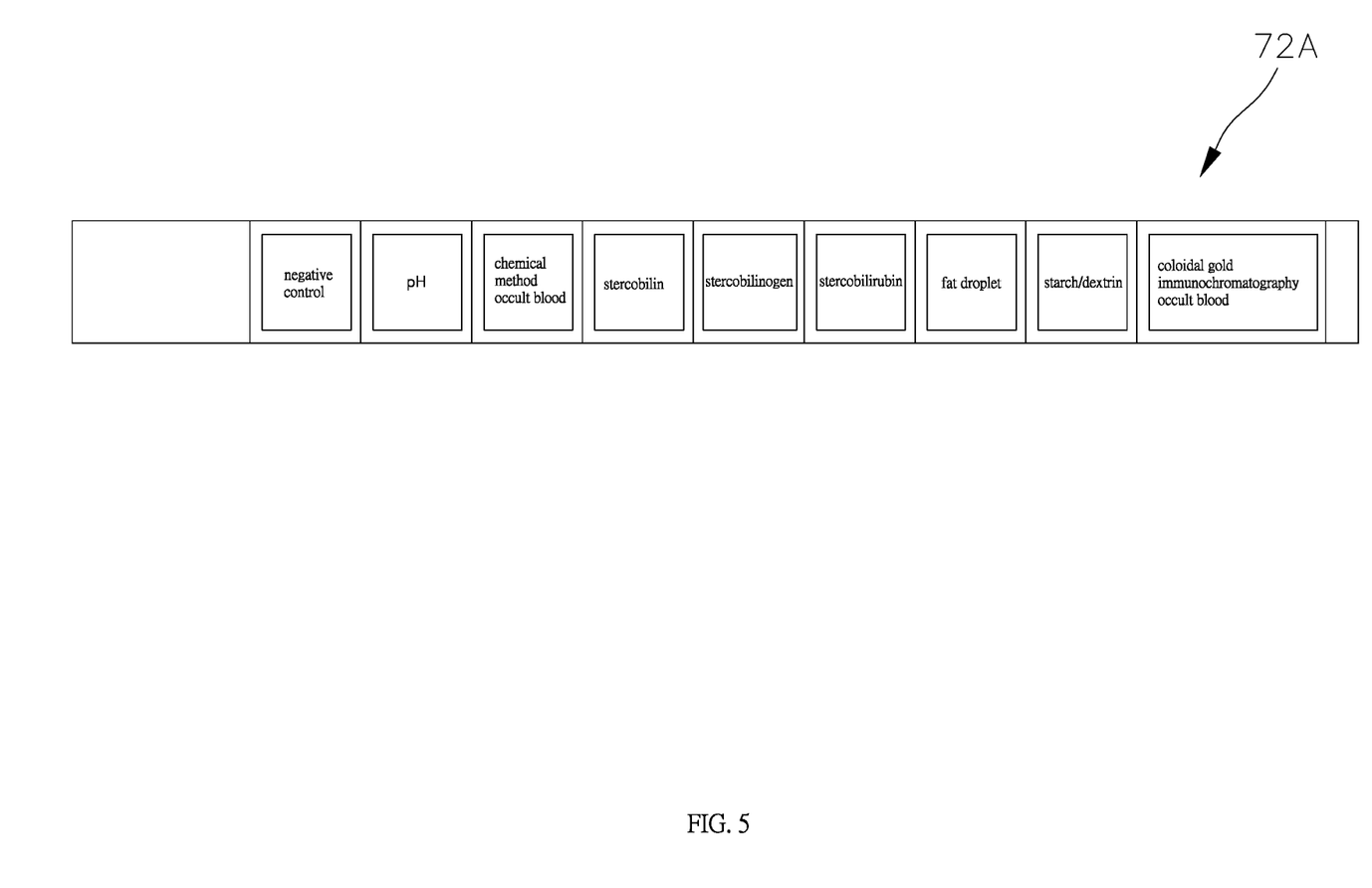
FIG. 5 is a schematic view of a second example of the integrated test film of the present invention.
Figure 6:
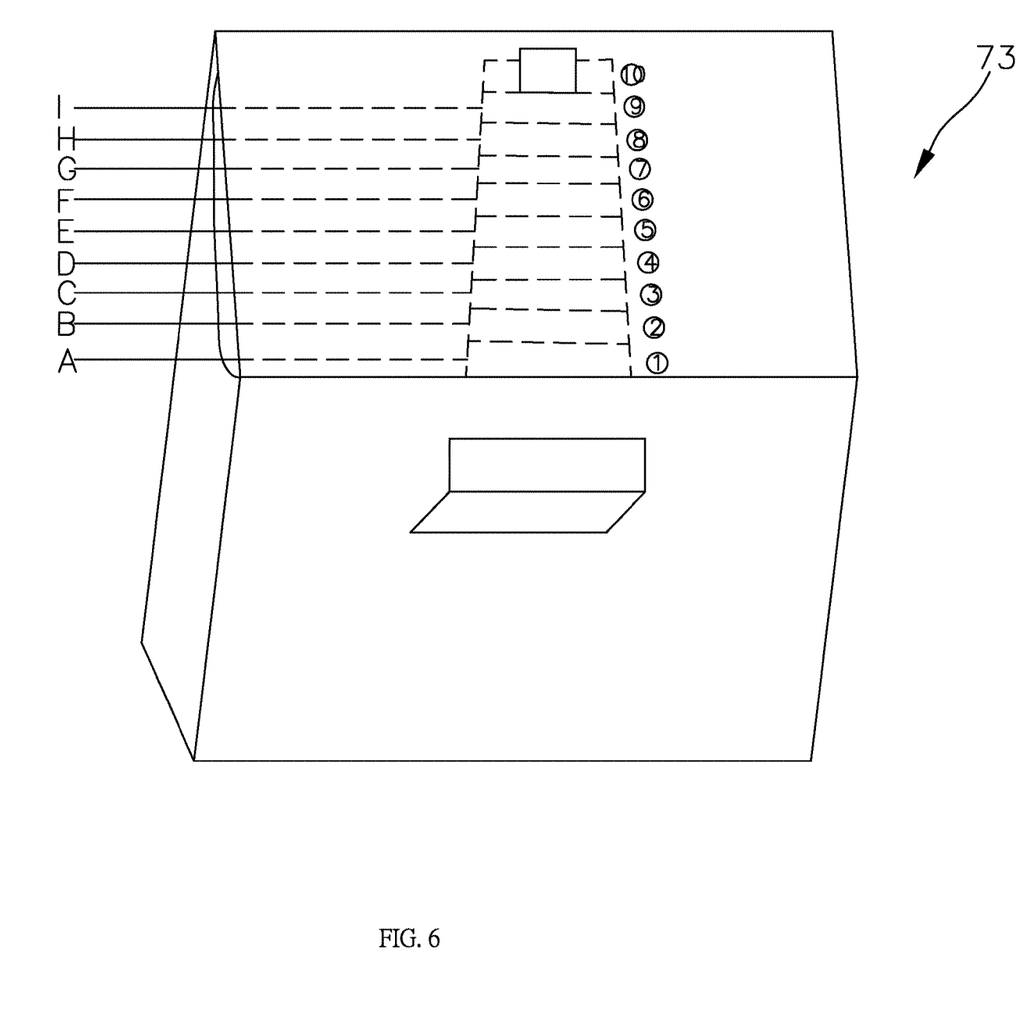
FIG. 6 is a schematic view of the spectrum scanning analyzer of the integrated test film of the present invention.

The integrated test film 72 consists of test papers for pH level, occult blood, stercobilin, stercobilinogen, stercobilirubin, fat droplet, starch and dextrin. The integrated test film 72 includes but is not limited to test papers for pH level, occult blood, stercobilin, stercobilinogen, stercobilirubin, fat droplet, starch and dextrin. The test film may be in strips or rings, and provides a negative control area on its parallel surface so as to eliminate the effect of the stool's own color on the result. The reagents required for various tests are absorbed on test papers of specific size, and such test papers are arranged in sequence and adhered on a hard and transparent film. When testing an excrement sample, the color reaction or tone corresponds to the excrement's pH value or related component content, and quantitative or semi-quantitative results are displayed.

PH test paper is used to test acidity/alkalinity of the excrement sample; guaiacol method or colloidal gold immunochromatography is used to test occult blood; Schmidt mercuric chloride test is used for detection of stercobilin; Ehrlich reaction is used to test for stercobilinogen; Harrison method is used to test for sterco-bilirubin; Sudan III method is used to test for fat droplet; and iodine colorimetry is used to test for starch and dextrin. The reagents required for various tests are absorbed on respective filter papers of specific size. Such filter papers are arranged in sequence and adhered on a hard and transparent film. When testing a stool sample, the color reaction or tone corresponds to the stool's pH value or related component content, and quantitative or semi-quantitative results are displayed.

As shown in FIG. 1 and FIG. 2, the excrement sample automatic cleaning device 9 is connected to the smart control panel 23 of the toilet seat 2 through a data cable, and is connected to the water storage tank 13 of the toilet bowl 1 through a pipe.

The design idea of the invention:

1. The toilet seat 2 is provided with the smart control panel 23 so that the user can selectively use the smart monitoring function or select specific items for excrement monitoring. The user identification system of the smart control panel 23 has uniqueness, such as fingerprints, voiceprints, scan codes, and the like. It helps the user to use different toilets or record the user's use when many users use the same toilet.

2. The illumination of the telescopic lifting device 3 at the rear end of the toilet seat 2 facilitates the clear photographing of the telescopic lighting and photographing device 8. The photograph shows the appearance and color of the excrement. Through the video and the recording time to know the frequency and ease of bowel movement, it is determined whether there are severe varicose veins around the anus or anal fissures to help determine a fecal blood source. The camera lens zooms in a certain times for photographing to observe whether or not the excrement has intestinal parasites or eggs, in part to replace the microscope checking of the excrement.

3. When the tray 31 of the telescopic lifting device 3 of the toilet bowl 1 is working, it is located in the back of the main chamber of the toilet bowl 1 and is located at a position of 2 centimeters higher than the water surface of the residual water of the toilet bowl for receiving the collected user's excrement. The front side of the tray 31 is curled to prevent the excrement from being contaminated with urine or the residual water in the chamber of the toilet bowl. The tray 31 is connected with the electronic weighing device 33 for measuring the weight of the excrement.

4. The smart control detection box may be disposed inside or outside the toilet bowl, or in the toilet seat.

The function case of the present invention:

Function Case I

If only bowel movement monitoring is selected, the telescopic lifting device 3 at the rear side of the toilet bowl 1 extends out and moves downward. The tray 31 is located at a position of 2 cm higher than the surface of the residual water in the chamber of the toilet bowl for receiving the collected user's excrement, thereby preventing the excrement from being contaminated with urine or the residual water in the chamber of the toilet bowl. The tray 31 is connected with the electronic weighing device 33. The rear end of the toilet seat 2 is provided with an LED light and a photographing device. The LED light provides appropriate lighting to capture high-clarity video for analysis and recording of frequency and ease of bowel movement, observation of changes in muscles and mucous membrane around the rectum during bowel movement, and observation of presence of parasite, eggs, fresh blood, pus, mucous and time of bowel movement, changes in appearance during bowel movement and time taken to complete bowel movement.

After bowel movement is completed, the tray 31 weighs the weight of the excreted excrement. When the toilet is flushed, the tray 31 is cleaned and retracted to the rear chamber of the toilet bowl. The weight and appearance of the excrement, dynamic video of muscles and mucous membrane around the rectum during bowel movement, dynamic video of excreted feces, time of bowel movement, and other data are output to the user's smart terminal or other storage device.

Function Case II

Bowel movement monitoring+excrement checking.

Bowel movement monitoring is the same as in functional case I.

At the end of bowel movement, select excrement checking function. Choose guaiacol method for detection of occult blood.

The excrement sample collection device 4 in the rear chamber of the toilet bowl 1 receives the instruction to extend out and collect excrement of about 15 to 45 grams as a sample. The excrement sample is sent to the sample container 61. The stirrer 62 in the sample container 61 mixes and pretreats the excrement sample. The integrated test film consisting of test papers for pH level, occult blood, stercobilin, stercobilinogen, stercobilirubin, fat droplet, starch and dextrin and the film consisting of blank test papers without containing test reagent are gripped by the robot 74 of the excrement sample detection and analysis device 7. The excrement sample is immersed in the sample container 61 for 10 to 15 seconds and then taken out, and sent to the test slot of the spectrum scanning analyzer 73 for scanning and testing. The scanning results are transmitted to the smart terminal 5 or the server. The test film is taken out and sent to the waste container 76. The excrement sample collection device 4, the sample container 62 of the excrement specimen preprocessing device 6, and the test slot of the spectrum scanning analyzer 73 are cleaned. The server processes the data, analyzes and interprets the data, proposes health guidance, or shares the data with a professional healthcare institution.

Function Case III

Bowel movement monitoring+excrement checking. Choose chemical method in "function case II" for occult blood detection and add immunochromatography for occult blood detection.

Bowel movement monitoring is the same as in functional case I.

Excrement sampling, pre-treatment and data processing are the same as in "function case II". Colloidal gold immunochromatography is added to the integrated test film on the basis of "function case II". Human monoclonal antibody is absorbed in the thin film, which is then immersed in excrement sample and placed in the test slot of the spectrum scanning analyzer 73 for scanning and detection. The scanned result is then transmitted to the smart terminal 5 or the server.

Two methods for testing fecal occult blood are used in the invention. Chemical method is less sensitive, does not differentiate red cells from food source and is affected by presence of drugs. Immunochromatography can eliminate interference of red cells from food source and drugs. Although it is highly sensitive, it may show false negative result when occult blood content is too high. The combination of the two methods will provide a more reasonable determination of result.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A smart toilet capable of monitoring excrement and urine, comprising a toilet bowl, a toilet seat, a telescopic lifting device, an excrement sample collection device, an excrement specimen preprocessing device, an excrement sample detection and analysis device, a telescopic lighting and photographing device, and a smart terminal;

the telescopic lifting device, the excrement sample collection device, the excrement specimen preprocessing device and the excrement sample detection and analysis device being installed in a space behind a toilet bowl body of the toilet bowl and above a suction channel;

the toilet seat including a flip-type toilet seat cover, a flip-type seat and a smart control panel; one end of each of the flip-type toilet seat cover and the flip-type seat being hingedly connected to the toilet bowl body of the toilet bowl, a user identification system being provided in the small control panel; the telescopic lifting device, the excrement sample collection device, the excrement specimen preprocessing device and the excrement sample detection and analysis device being connected with the smart control panel of the toilet seat through data cables;

the telescopic lighting and photographing device being mounted to a rear side of the flip-type seat;

the smart terminal receiving data transmitted from a data processor through a wireless transmission and performing analysis and interpretation;

the telescopic lifting device including a tray, a telescopic mechanism and an electronic weighing scale; the tray being mounted on a top of the electronic weighing scale, the electronic weighing scale being mounted on an outer end of the telescopic mechanism, an inner end of the telescopic mechanism being fixed in the space behind the toilet bowl body of the toilet bowl, the outer end of the telescopic mechanism, equipped with the tray, passing through a hole that can be opened and closed on a rear wall of the toilet bowl body and extending to a position above the surface of residual water in the toilet bowl;

the excrement sample collection device including a telescopic connecting arm and a hollow semi-circular tube with a sensor; the hollow semi-circular tube being installed at a front end of the telescopic connecting arm, the hollow semi-circular tube being located above the tray of the telescopic lifting device, a rear end of the telescopic connecting arm being fixed in the space behind the toilet bowl body of the toilet bowl;

the excrement specimen preprocessing device including a sample container, a stirrer and a water injection pipe; the sample container being located at a distal end of a movement path of the hollow semi-circular tube of the excrement sample collection device so as to receive excrement; the stirrer having rotatable stirring blades mounted in the sample container, one end of the water injecting pipe extending into the sample container, another end of the water injecting pipe being connected to a water source;

the excrement sample detection and analysis device including the data processor, an integrated test film, a spectrum scanning analyzer, a robot, a test film storage container and a waste container; the data processor, the integrated test film, the spectrum scanning analyzer, the robot, the test film storage container, the waste container and the robot being installed in the space behind the toilet bowl body of the toilet bowl, a first working position of the robot being located at the test film storage container on which the integrated test film is placed, a second working position of the robot being located at the sample container of the excrement specimen preprocessing device, a third working position of the robot being located at the spectrum scanning analyzer, a fourth working position of the robot being located at the waste container, the robot moving among the four working positions; the spectrum scanning analyzer being connected to the data processor through one of the data cables for providing a scanning image to the data processor.

2. The smart toilet capable of monitoring excrement and urine as claimed in claim 1, wherein the integrated test film consists of test papers for pH level, occult blood, stercobilin, stercobilinogen, stercobilirubin, fat droplet, starch and dextrin.

3. The smart toilet capable of monitoring excrement and urine as claimed in claim 1, further comprising an excrement sample automatic cleaning device; the excrement sample automatic cleaning device being installed in the space behind the toilet bowl body of the toilet bowl and above the suction channel, the excrement sample automatic cleaning device being connected to the smart control panel of the toilet seat through one of the data cables and connected to the water storage tank of the toilet bowl through a pipe.

* * * * *